(12) United States Patent
Acher et al.

(10) Patent No.: US 8,444,707 B2
(45) Date of Patent: *May 21, 2013

(54) EPILATORY STRIP

(75) Inventors: David Acher, Hull (GB); Frederic De La Torre, Hull (GB); Marielle De La Torre, Hull (GB); Candice Monge, Hull (GB)

(73) Assignee: Reckitt Benckiser (UK) Limited, Slough, Berkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/099,852

(22) Filed: May 3, 2011

(65) Prior Publication Data

US 2011/0208208 A1 Aug. 25, 2011

Related U.S. Application Data

(63) Continuation of application No. 10/502,680, filed as application No. PCT/GB03/00653 on Feb. 12, 2003, now abandoned.

(30) Foreign Application Priority Data

Feb. 13, 2002 (GB) .................... 0203395.9

(51) Int. Cl.
*C14C 1/06* (2006.01)

(52) U.S. Cl.
USPC .............................................. 8/160

(58) Field of Classification Search
USPC .............................................. 8/160
See application file for complete search history.

(56) References Cited

U.S. PATENT DOCUMENTS 3,981,681 A * 9/1976 de la Guardia .................. 8/161
4,282,877 A * 8/1981 Mathews ...................... 606/134

FOREIGN PATENT DOCUMENTS

GB 474102 * 10/1937
GB 2336535 * 10/1999

OTHER PUBLICATIONS

Ehlers et al, Females have lower skin surface pH than men, May 2001, Skin Research and Technology, vol. 7, Issue 2, 1 page (abstract).*
Davis, Tinsley, Re: How does the pH of the skin serve as a barrier against bacteria?, Apr. 8, 1999, MadSci Network, 1 page.*
Cabot Sanmar Limited, A rare fusion, Jun. 2005, http://www.sanmargroup.com/brochures/CabotJuly-05.pdf.*

* cited by examiner

*Primary Examiner* — Daniel Sullivan
*Assistant Examiner* — Trevor Love
(74) *Attorney, Agent, or Firm* — Norris McLaughlin & Marcus PA

(57) ABSTRACT

A preformed epilatory strip comprises a matrix material that includes a mixture of a major amount—at least 60 wt %—of a sugar-based material and a minor amount—1 to 30 wt %—of a rosinous material. Optionally a particulate material, for example fumed silica, is present.

8 Claims, No Drawings

EPILATORY STRIP

The present application is a Continuation application of U.S. Ser. No. 10/502,680, which in turn was an application filed under 35 USC 371 of PCT/GB03/00653.

This invention relates to a preferred epilatory strip, its manufacture and use.

Epilatory compositions formed of viscoelastic materials are well known. The viscoelastic materials may in certain embodiments be rosin-based. In other embodiments they may be sugar-based. A tackifier, such as colophony, may be included to make them sticky.

In some products the epilatory compositions may be supplied in the form of strips, retained between cellophane sheets. The cellophane sheets may have coatings of polyvinyl chloride, which acts as a barrier preventing the composition, or components of it, from migrating through the sheets; and also having the correct adhesive properties for use. In use, the user peels away one of the cellophane sheets, presses the epilatory strip firmly onto the area to be plucked, then pulls one end of the remaining cellophane sheet sharply away from the area. The hairs trapped in the composition are removed from the treated area along with, optimally, all of the composition, still attached to the remaining backing strip.

In an alternative approach a composition may be warmed, and then applied to the skin by means of a spatula or other applicator. Strips of fabric are then applied so that they adhere to the epilatory composition. The strips are then pulled sharply to remove the epilatory material, and hair, from the skin.

In both approaches the viscoelastic properties of the compositions are important. However this is particularly so in the case of the compositions supplied as strips, since these are applied to the skin at ambient temperature. At ambient temperature the compositions should be soft and pliable, such that they mould closely to the body shape. On the other hand they must not be so soft that they flow prior to use. When they are in place on the body and the user pulls the remaining backing strip, applying a high frequency strain rate to the compositions, their elastic properties should predominate over their viscous properties.

There is a particular problem with known compositions supplied in the form of strips, in meeting one of the requirements described in the previous paragraph. It is that under warm ambient conditions the compositions may flow, and leak out from between the sheets. One approach to counter this has been to supply strips with considerably over-sized cellophane sheets. However, clearly, this approach is inadequate as a solution to a situation where there might be a substantial flow of a composition. It is also inefficient in terms of materials and transportation, and undesirable from a marketing perspective, in that consumers perceive that such a product is of poor value.

Epilatory compositions, particularly compositions supplied in the form of strips, may include a non-aqueous based aliphatic or aromatic resin, for example a rosinous material. Suitably, such compositions may exhibit strong adhesive properties which render them suitable to trap and remove hairs from a treated area. However, there are particular disadvantages associated with known non-aqueous based aliphatic or aromatic resins. Notably, as a consequence of the strong adhesive properties of these resins, skin as well as hairs may be removed from the treated area, thereby causing discomfort and irritation for the user. Suitably, it may be undesirable for users having sensitive skin to use such compositions and/or to use such compositions on sensitive parts of the body. Moreover, such resins may bond strongly with the skin and the resin may separate from the strip when the strip is pulled from the treated area, thereby leaving a deposit of the resin on the skin. It is typically difficult to remove such a resinous deposit merely by rinsing the treated area with water, because of the non-aqueous characteristics of the resin. Suitably, in order to remove the resin from the treated area, it is typically necessary to wipe the treated area with a cloth impregnated with an organic solvent mixture that dissolves and/or loosens the resin. Such a procedure not only involves applying an organic solvent to the skin which may cause further discomfort and/or irritation, but also it is inconvenient and creates unnecessary additional expense for the user.

In an attempt to overcome the aforementioned problems associated with epilatory compositions including non-aqueous based resins, attention has focused on compositions that include aqueous based materials, such as sugar-based materials. Suitably, a deposit of an aqueous based composition left on a treated area following removal of a strip may be rinsed more easily from the area using water compared to a non-aqueous based epilatory composition, thereby reducing or negating the need to use a cloth impregnated with an organic solvent. However, aqueous based materials typically exhibit lower adhesive properties than non-aqueous based resins. Suitably, aqueous based materials may be less effective at removing hairs from a treated area than non-aqueous based resins.

The present invention seeks to solve the aforementioned problems associated with an epilatory composition.

According to a first aspect, the present invention provides a preformed epilatory strip comprising a matrix material that includes a mixture of a sugar-based material and a rosinous material, wherein the sugar-based material provides at least 60% of the weight of the epilatory strip and the rosinous material comprises from 1 to 30% of the weight of the epilatory strip.

Suitably, the epilatory strip of the present invention may exhibit improved adhesive properties compared to a comparable epilatory strip including a sugar-based material alone. Suitably, the epilatory strip of the present invention may be more effective at removing hair from a target area than a comparable epilatory strip including a sugar-based material alone. Suitably, the epilatory strip of the present invention may be rinsed more easily from the skin with water compared to an epilatory strip including a rosinous material alone. Consequently, it is typically not necessary to employ specialist cloths impregnated with an organic solvent to remove deposits of the epilatory strip of the present invention from the skin.

The matrix material is suitably a gel-like material with adhesive properties.

Suitably, the sugar-based material of the matrix material, is formed by heating sugar(s) with acids (such as citric acid) as disclosed in GB 901624, GB 1242083, GB 2231494A, and GB 2157951A.

Preferably, the sugar-based material constitutes at least 70% by wt, more preferably at least 75% by wt, of the epilatory strip.

Suitably, the sugar-based material constitutes up to 95% by wt, preferably up to 92.5% by wt, more preferably up to 90% by wt, more preferably up to 88% by wt, of the epilatory strip of the present invention. Most preferably it constitutes up to 80% by wt, of the epilatory strip.

Preferably, the rosinous material is rosin and/or a rosin based material. Most preferably, the rosinous material is a rosin ester and/or colophony and/or a rosin acid.

Suitably, the rosinous material comprises at least 3% by wt, more preferably at least 5% by wt, and most preferably at least 7.5% by wt, of the epilatory strip.

Preferably, the rosinous material comprises up to 25% by wt, more preferably up to 20% by wt, most preferably less up to 18% by wt, and especially up to 12% by wt, of the epilatory strip of the present invention.

Unexpectedly, it has been found that by including a rosinous material in the epilatory strips of the present invention within the aforementioned defined limits then the adhesive properties of the sugar-based material may be significantly enhanced while maintaining its water rinsability characteristics.

Suitably, the weight ratio of sugar-based material to rosinous material in the epilatory strip of the present invention is less than or equal to 19:1, preferably less than or equal to 15:1, preferably less than or equal to 13:1, preferably less than or equal to 10:1.

Suitably, the weight ratio of sugar-based material to rosinous material in the epilatory strip of the present invention is greater than or equal to 2.3:1, preferably greater than or equal to 3:1, more preferably greater than or equal to 4:1, most preferably greater than or equal to 5:1.

Preferably the rosinous material comprises a separate phase from the sugar-based material, preferably a phase dispersed within the sugar-based material, the latter being a continuous phase. However the rosinous material may nevertheless be partially partitioned within the sugar-based phase.

Preferably, the rosinous material comprises droplets, which may be of any shape, dispersed within the matrix material. Typically, the droplets are spherical and/or ellipsoidal in shape.

Suitably, the average maximum cross-sectional dimension of the droplets of rosinous material, as measured by photon correlation spectroscopy, is greater than or equal to 20 nm, more preferably greater than or equal to 30 nm, most preferably greater than or equal to 40 nm, especially greater than or equal to 50 nm.

Suitably, the average maximum cross-sectional dimension of the droplets of rosinous material, as measured by photon correlation spectroscopy, is less than or equal to 5000 nm, preferably less than or equal to 1500 nm, preferably less than or equal to 1000 nm, most preferably less than or equal to 500 nm.

Generally, smaller droplets are believed to give better performance. Preferably 90% of particles are of size (measured as indicated above) in the range 200-2000 nm.

Shear mixing may be effected to "cut" the rosinous material and reduce the droplet size.

Preferably the epilatory strip is of a so-called "cold" epilatory composition (that is, one which can be applied at ambient temperature without reheating).

Preferably, the epilatory composition of the present invention further includes a particulate material in admixture with the matrix material.

Preferably the particulate material is a colloidal material. Preferably it has particles of mean diameter 1-200 nm, more preferably 5-100 nm, and most preferably 10-50 nm.

Preferably the particles are present in the epilatory strip in an amount of at least 1% wt/wt, more preferably at least 2% wt/wt, and most preferably at least 3% wt/wt. Suitably they are present in an amount up to 40% wt/wt, preferably up to 20% wt/wt, and most preferably up to 10% wt/wt.

Preferred particulate materials for use in the present invention are siliceous materials. Especially preferred is fumed silica.

Fumed silica is currently manufactured in a process that involves flame hydrolysis of silicon tetrachloride, in an oxyhydrogen flame. It is a colloidal form of silica having silanol groups, able to participate in hydrogen bonding. Fumed silica typically comprises colloidal particles of mean diameter 1-200 nm. Preferably the fumed silica is of mean diameter 5-100 nm, more preferably 10-50 nm. The external surface area is typically in the range 15-380 m$^2$/g. Fumed silicas are typically non-porous and thus have no internal surface area. They may be hydrophobic and of use in the present invention but preferred fumed silicas for use in the present invention are hydrophilic.

Preferred particulate materials are believed to locate at interfaces between the rosinous material and the sugar-based material. Preferably it helps to maintain a gel structure and prevents coalescence of the rosinous material.

Preferably, the epilatory strip of the present invention further includes a branched polyalkene.

The branched polyalkene is suitably a polyalkene having $C_{1-4}$ alkyl groups, preferably methyl groups, projecting from a carbon backbone. Preferably the branched polyalkene comprises units derived from isobutene. These may have been homopolymerised, to form polyisobutene, or may have been copolymerised with other unsaturated materials, preferably other alkenes.

The branched polyalkene when used may be fully saturated. Thus, the polymer may be hydrogenated in order to render the compounds saturated at their ends. However polyalkenes which have unsaturated end groups are also suitable, and are generally preferred.

The branched polyalkene may be regarded as a polymer having a carbon backbone carrying a proportion of pendent alkyl groups, preferably methyl groups. Preferably the carbon backbone carries both hydrogen atoms and pendent groups. The numerical ratio of pendent alkyl groups to hydrogen atoms on the backbone is suitably in the range 0.1:1-10:1, preferably 0.5:1-3:1, and most preferably 0.8:1-1.2:1 (such hydrogen atoms are directly on the backbone; hydrogen atoms within the pendent alkyl groups are not included). Especially preferred is a ratio of substantially 1:1, as is obtained with homopolymeric isobutene, whose repeat unit is —$[CH_2-C(CH_3)_2]_n$—.

One preferred branched polyalkene material is hydrogenated polyisobutene, a readily available material currently used in cosmetics. Grades are available under the trade marks POLYSYNLANE and PARLEAM, from Rossow Cosmetiques, France, or from N of Corporation, Japan.

One especially preferred branched polyalkene material is non-hydrogenated polyisobutene, a readily available material currently used in cosmetics. Grades are available under the trade mark INDOPOL, from BP Chemicals, UK.

Suitably the branched polyalkene provides up to 20% of the total weight of the strip, preferably up to 15%, more preferably up to 10%, and most preferably up to 5%. Especially preferred is an amount up to 3% of the total weight of the strip.

Suitably the branched polyalkene when used provides at least 0.1% of the total weight of the strip, preferably at least 0.5%, most preferably at least 0.9%.

Suitably the branched polyalkene has a weight average molecular weight in the range 400 to 100,000, preferably 1,000 to 30,000, more preferably 1,500 to 10,000.

The branched polyalkene may be in the nature of a highly viscous liquid.

Preferably the branched polyalkylene is in the nature of a waxy or tacky solid or semi-solid.

We have found that the inclusion of a branched polyalkylene in an epilatory strip of the adhesive type produces a valuable skin care benefit, even when present in a small amount. The benefit is such that the irritation which certain epilatory compositions can elicit in some users is eased, or avoided altogether. Excellent adhesive and viscoelastic properties are also achieved.

The epilatory strip may suitably comprise up to 40% by weight, preferably up to 20% by weight, of other components, which may include one or more of a natural wax, a fragrance, a polymer, an essential oil, a silicone oil, a colorant, an antioxidant or a paraffin or mineral oil.

Suitably, the epilatory strip of the present invention, particularly an epilatory strip including a particulate material in admixture with the matrix material, when not under applied stress, may be shape-stable for a period of 6 months at all temperatures in the range 20-50° C.

Suitably, the epilatory strip of the present invention, particularly an epilatory strip including a particulate material in admixture with the matrix material, when not under applied stress, may be shape-stable for a period of 6 months at all temperatures in the range 20-50° C.; whereas the corresponding strip not containing any said particles, when not under applied stress, flows under its own weight at least some temperatures in the range 20-50° C. during a period of 6 months.

Suitably, the epilatory strip of the present invention, particularly an epilatory strip including a particulate material in admixture with the matrix material, is such that its elastic modulus may exceed its viscous modulus at all frequencies up to 0.1 rad/s at 50° C., more preferably all frequencies up to 1 rad/s at 50° C., most preferably at all frequencies up to 2 rad/s at 50° C.

In certain embodiments, notably epilatory strips including a particulate material, the elastic modulus may exceed the viscous modulus at all frequencies up to 20 rad/s at 50° C.

Preferably at certain higher frequencies (representative of the rapid removal of the epilatory strip from the user's skin), the elastic modulus also exceeds the viscous modulus, at temperatures within the temperature range 20-50° C.

Preferably the elastic modulus exceeds the viscous modulus (when measured at 35° C.) at a frequency of at least 10,000 rad/s, more preferably at a frequency at least 5,000 rad/s.

Thus, preferably the epilatory strip, especially an epilatory strip including a particulate material, is such that, at ambient temperatures, at low frequencies of applied stress the elastic modulus exceeds the viscous modulus; at high frequencies of applied stress the elastic modulus exceeds the viscous modulus; and at moderate frequencies, in between, the viscous modulus exceeds the elastic modulus. The epilatory strip in transit and storage corresponds to the low frequency condition, and the non-viscous nature of the strip aids shape stability in storage and transit; the application of the epilatory strip to the skin corresponds to the moderate frequency condition, and the viscous nature of the strip aids application and good contact with hair and skin; and pulling the epilatory strip sharply from the skin corresponds to the high frequency condition, the non-viscous, glassy nature of the strip aiding effective hair removal. The transition between the low frequency condition and the moderate frequency condition is known as the gel point. The transition between the moderate frequency condition and the high strain rate condition is known as the glass transition.

The elastic modulus G' (sometimes known as the storage modulus) corresponds to the energy which can be stored and released by a bulk material. The viscous modulus G" (sometimes known as the loss modulus) corresponds to the energy dissipated by a bulk material due to friction between its macromolecules when it is deformed.

$$G' = \frac{\sigma_o}{\gamma_o}\cos\delta$$

$$G'' = \frac{\sigma_o}{\gamma_o}\sin\delta$$

wherein $\sigma_o$ is the stress amplitude, $\gamma_o$ is the strain amplitude and $\delta$ is the out-of-phase coefficient.

The measurements quoted later are based on studies carried out into the rheology of the viscoelastic compositions in order to obtain a better understanding of their adhesive behaviour and their suitability as epilatory materials. These studies involved subjecting the materials to dynamic investigations in which a sinusoidal strain at defined frequencies was applied to the materials and the resulting output force was measured. In these studies a stress control rheometer was used, the SR rheometer commercially available from the company Rheometrics, using parallel plate geometry of 25 mm in diameter. The output force was found to include an in-phase elastic component G' and an out-of-phase viscous component G". The output force can be expressed as follows.

$$\sigma = \sigma_o \sin(t\omega + \delta)$$
$$= \sigma_o \cos\delta \sin t\omega + \sigma_o \cos\delta \cos t\omega$$

where $\omega$ is the test frequency and t is the time.

Within the linear stress-strain domain of the material G' is desirably lower than G" at moderate frequency oscillation in order to prevent the material cracking and to ensure that the material has strong adhesion at the material/hair interface. The values of G' and G" at moderate frequency oscillation are a measure of how readily the material wets the hairs. Moderate frequency oscillation is a long time process and corresponds to the time when the material is being applied to the skin. The lower values of G' and G" at this moderate frequency, the better the material wets the hairs. Thus the hairs become well embedded in the material in a very short time (ie the time needed for spreading the strip on the skin). However G' should be higher than G" at high frequency oscillation (which mimics the action of the user in rapidly pulling the strip from the body) in order to remove hairs efficiently. Also, at low frequency oscillation, or no oscillation, G' is preferably higher than G", in accordance with this invention, in order to obtain the benefit of enhanced stability, even when warm.

The definitions given herein refer to stresses applied to the material within its linear stress-strain domain, which may typically be up to a few thousand Pa.

Preferably, therefore, the composition of the strip is of an elastic nature, when unstressed.

Preferably, therefore, the composition of the strip is of a viscous nature when moderately stressed, for example on application to the skin.

Preferably, therefore, the composition of the strip is of an elastic nature when highly stressed, for example on removal from the skin (as by abrupt pulling).

By ensuring that the epilatory strip satisfies the above parameters, it can be readily applied to the skin at body temperature, yet it is very efficient at removing hairs from the skin and, surprisingly, the user experiences less pain.

References in this specification to a strip not under applied stress are to the strip, resting on a horizontal surface.

Whilst we are not bound by any theory, we believe that when the epilatory strip includes a particulate material, the particles form a network throughout the epilatory strip, providing a structure or backbone which inhibits the flow of the strip, under warm conditions.

Preferably, the epilatory strip is supplied sandwiched between backing sheets, for example of cellophane, or paper or another non-woven material. In use, one sheet is removed from a strip of epilatory composition and that strip is then applied to the skin with the remaining sheet uppermost. The end of that sheet is grasped and pulled sharply, to remove the epilatory strip from the skin, along with hairs with which it is in contact. In other embodiments that upper backing sheet is intended to be peeled away, and a fabric is applied to the epilatory strip, and is used to pull the epilatory strip sharply from the skin.

Because the epilatory strip, particularly an epilatory strip including a particulate material, does not flow even under very warm ambient conditions it may be applied to a backing sheet during manufacture so as to cover a larger area of the backing sheet, than has been achieved, with prior epilatory strips. Preferably the strip covers at least 60% of the area of the backing sheet, more preferably at least 80%, most preferably at least 90%.

Preferably an epilatory strip of the invention is of an acidic material, for example having a pH in the range 2-7, more preferably 4.5-6.5, most preferably 5-6.

Preferred epilatory strips of the present invention are such that residues are removable from the user's skin by normal water washing.

A preferred epilatory strip of the present invention comprises:
at least 60% wt of a sugar-based matrix material;
1-30% wt of a rosin-based matrix material;
0.1-20% wt of a branched polyalkene;
1-20% wt of a particulate material; and
optionally up to 40% wt of additional components.

An especially preferred epilatory strip of the present invention comprises:
at least 70% wt of a sugar-based matrix material;
2-20% wt of a rosin-based matrix material;
0.5-5% wt of a branched polyalkene;
1-5% wt of a particulate material; and
optionally up to 20% wt of additional components.

In accordance with further aspects there are provided a method of manufacturing a preferred epilatory strip, as defined above; and a method of epilation, using such preformed epilatory strips.

The invention will now be further described, by way of example.

EXAMPLE 1

A composition for manufacture of an epilatory strip was made with the following ingredients.

| Ingredients Inverted sugar base: | % wt/wt |
| --- | --- |
| Sugar (sucrose) | 78.3 |
| Citric acid monohydrate | 1.3 |
| DERMULSENE RA 405 | 1.5 |
| Water | 7.4 |
| DERTOLINE RC2 rosinous material | 7 |
| HDK N20 fumed silica | 2 |
| PARLEAM SV polyisobutene | 1 |
| KOH (50% in water) | 1.5 |

DERMULSENE RA 405 is a collophonium emulsion (rosin acid) available from DRT-Granel.
DERTOLINE RC2 is a colophonium derived resin, glycerol rosinate, available from DRT-Granel
HDK N20 is a fumed silica powder available from Wacker.
PARLEAM SV, also called POLYSYNLANE SV, is an hydrogenated polyisobutene polymer available from Rossow Cosmetiques, France. The SV grade denotes the super high viscosity grade.

Method of Manufacture
1. Preparation of an Inverted Sugar-Based Material:
    a. Prepare an inverted sugar (sugar/citric acid/water)—cool down to 60° C. and maintain the tank temperature at 60° C. during the process;
    b. Add the DERMULSENE RA 405 and mix slowly during 30 minutes;
    c. Adjust the viscosity of the mix to 130 Pa·s (at a reference temperature of 35° C.) by adding water.
2. Dispersion of Rosin and PARLEAM SV in the Sugar Base
    a. Add the PARLEAM SV previously preheated in the oven at 60° C., to the inverted sugar-based material from Step 1, and incorporate it by mixing;
    b. Then add the DERTOLINE RC2 previously preheated in the oven at 60° C. and incorporate it by mixing;
3. Formula Gelation
    a. Add the HDK N20 and homogenise using a high speed turbine at 10 rpm.
    b. Add the potassium hydroxide under stirring. The resulting composition at ambient temperature had the appearance of a viscous gel.
4. Formula Characterisation
    a. pH of the composition (dilute 50% in water)=5.6
    b. gel point at 35° C. (G'=G")=18 rad/s
    c. viscosity at 35° C.=210 Pa·s The resulting gel product could be formed in standard manner into water rinsable cold wax strips.

Being only mildly acidic the composition is particularly suitable for sensitive skin. To this end, it is predominantly sugar-based; the rosinous material content is low (but sufficient to promote good performance); and it contains PARLEAM SV.

Preliminary tests indicate that the composition does not flow at high temperatures such as would be found during summer months in warm countries, and that other required properties are very good. The PARLEAM SV component appears not to have caused any adverse effect on the properties of the composition.

EXAMPLE 2

A composition for manufacture into an epilatory strip was made with the following ingredients.

| Ingredients Inverted sugar base: | % wt/wt |
| --- | --- |
| Sugar (sucrose) | 77.6 |
| Citric acid monohydrate | 1.3 |
| DERMULSENE RA 405 | 1.3 |
| Water | 7.4 |
| TEG rosinate | 4.84 |
| DERTOLINE RC2 rosinous material | 2.16 |
| INDOPOL H2100 polyisobutene | 1 |
| KOH (50% in water) | 1.4 |

TEG rosinate is triethylene glycol rosinate available from DRT-Granel.

INDOPOL H2100 is non-hydrogenated polyisobutene, molecular weight approx. 2,000, available from BP. Being non-hydrogenated it has unsaturation at the polymer termini.

The epilatory composition was prepared by the method described in Example 1, except:

In Step 1 the temperature was 65° C.

In Step 2 both rosinates and the polyisobutene were pre-mixed in a separate tank and added to the inverted sugar material at 65° C. Homogenisation for 5 minutes using a high speed turbine operated at 1,000 rpm ensured good dispersion of the rosinates.

In Step 3a. the fumed silica was blended in using a high speed rotor/stator mixer/pump operated at 1,000 rpm for 15 minutes.

In Step 3b. the KOH was added in a single addition with stirring. The composition was then recirculated in the high speed rotor/stator mixer/pump. Friction increased the temperature to 80° C.

The gel point of the Example 2 composition, measured at 50° C., is 25 rad/s. Its viscosity, measured at 35° C., is 230 Pa·s. Its pH is 5.5.

The invention claimed is:

1. A preformed epilatory strip sandwiched between sheets of a non-woven material, the epilatory strip comprising a matrix material which comprises:
    at least 60% wt. of a sugar-based material;
    1-30% wt. of a rosinous material;
    0.1-5% wt. of a branched polyalkylene;
    1-5% wt. of a particulate material; and,
    optionally a balance of one or more additional components, and wherein the matrix material is a gel which, when not under applied stress, is shape-stable for a period of 6 months at all temperatures in a range 20-50 C,
wherein the matrix material has an elastic modulus that exceeds a viscous modulus of the matrix material (i) at all frequencies up to 20 rad/s at 50 C and (ii) at a frequency of at least 5,000 rad/s at 35 C, wherein the matrix material has a pH between 5-6.

2. A preformed epilatory strip according to claim 1,
    wherein the rosinous material constitutes between 5 and 20% of the weight of the epilatory strip.

3. A preformed epilatory strip according to claim 1, wherein the rosinous material comprises droplets dispersed in the sugar-based material.

4. A preformed epilatory strip according to claim 3, wherein the average maximum cross-sectional dimension of the droplets of rosinous material is less than or equal to 500 nm.

5. A preformed epilatory strip according to claim 1, wherein the particulate material is colloidal.

6. A preformed epilatory strip according to claim 1 wherein the particulate material is a siliceous material.

7. A preformed epilatory strip according to claim 1, wherein the particulate material is fumed silica.

8. A performed epilatory strip according to claim 1, wherein the particulate material is present at a concentration greater than 1% wt. and less than 5% wt.

* * * * *